US00PP09988P

United States Patent [19]

McGourty

[11] Patent Number: Plant 9,988

[45] Date of Patent: Aug. 5, 1997

[54] PLANT NAMED 'HILLSIDE BLACK BEAUTY'

[76] Inventor: Mary Ann McGourty, P.O. Box 614, Norfolk, Conn. 06058

[21] Appl. No.: 547,709

[22] Filed: Oct. 19, 1995

[51] Int. Cl.[6] ..... A01H 5/00

[52] U.S. Cl. ..... Plt./68.1

[58] Field of Search ..... Plt./68.1

[56] References Cited

PUBLICATIONS

Griffiths, Mark, "*C. ramosa*" *Index of Garden Plants, R.H.S.*, London p. 252 (date unknown).

*Primary Examiner*—James R. Feyrer

[57] ABSTRACT

A variety of *Cimicifuga ramosa* having leaves with dark coloration.

1 Drawing Sheet

SUMMARY OF THE INVENTION

The new variety of Cimicifuga is a hybrid from an unnamed purple-leaf plant of *Cimicifuga ramosa*. I originally discovered the plant growing in a cultivated state in my home garden. This plant is easily distinguished by the intense darkness of the leaf color, when compared with other known plants of *Cimicifuga ramosa*. Continued observation led to a greater recognition of the uniqueness of the plant. It is distinctly darker purple in leaf color than 'Brunette', which has heretofore been generally acknowledged as the darkest leaf form, when the two are grown under the same cultural conditions in the garden. The new variety has been asexually reproduced by me by division of the rootstock, and it is hereby named *Cimicifuga ramosa* 'Hillside Black Beauty'.

BRIEF DESCRIPTION OF THE ILLUSTRATIONS

The invention is illustrated in the attached photographs in which.

DETAILED DESCRIPTION OF PREFERRED EMBODIMENT

Figure 1:
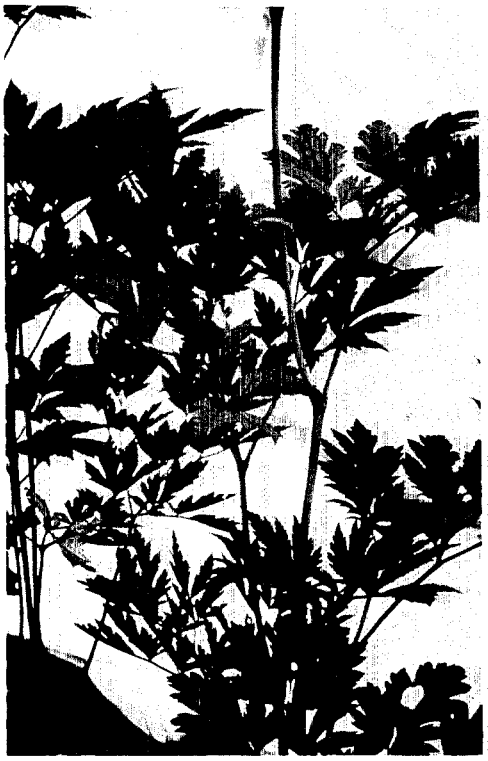
FIG. 1 shows a plant with very dark purplish-black leaves.
Figure 2:
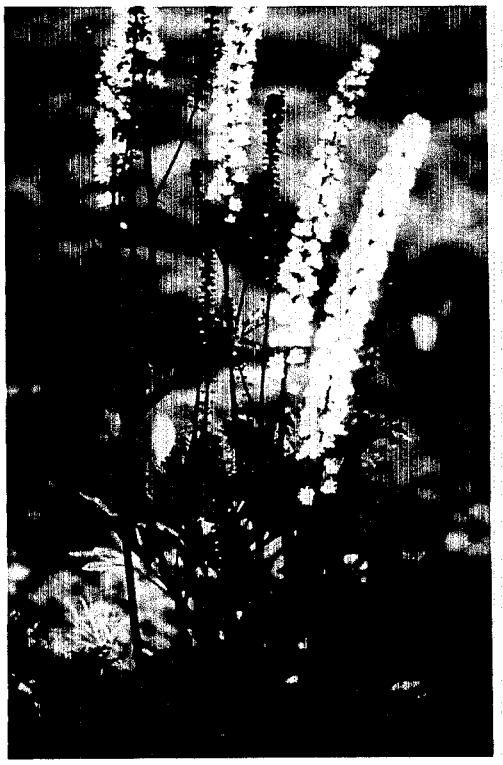
FIG. 2 shows a plant with very dark stems and buds, opening to white flowers with a pale blush pink tinge. The colors are as true as it is possible to secure through color photography.

The species *Cimicifuga ramosa* is a clump-forming herbaceous perennial of upright growth habit with stems approximately four and one-half (4½) feet to seven (7) feet in height. The leaves are ternate; leaflets are oblong-oval, biserrate, veins reticulate, impressed. Leaves vary in size from twelve (12) to eighteen (18) inches in length and from ten (10) to fourteen (14) inches in width, depending on cultural conditions. Flowers are small (up to e,fra 1/2" in diameter), many (up to 220) in racemes from ten (10) to fourteen (14) inches in length. The dimensional and flower number depend on environmental conditions and cultural practices, and therefore may be slightly small or greater. The flowers bloom in Connecticut from early September to early October. Flower characteristics and fragrance are identical to those of the parent species, except for color.

The species *Cimicifuga ramosa* is quite uniform in appearance and does not have a large number of varieties of subspecies. A few variants with slight or moderate purple cast to the leaves have been given distinct variey names. The principal form of the plant is generally known by the species name *Cimicifuga ramosa;* see *The New Royal Horticultural Society Dictionary of Gardening, Index of Garden Plants,* edited by Mark Griffiths, 1994, page 252, (copy attached).

The new variety shares the foregoing chracteristics with its parent, but it is a unique and improved form of the original plant species, *Cimicifuga ramosa,* in one principal aspect. The new variety is a distinct and stable form with intense dark purple color to the leaves, stems and flower buds.

The present invention has leaves a color between Brown 200A and Greyed-Purple 187A, the darkest purple color on The Royal Horticultural Society Colour Chart. The stems are Greyed-Purple 187A, and they have a glaucous bloom that can be rubbed off. The tight buds (sepals) are Greyed-Purple 187A as defined by The R.H.S. Colour Chart. Although the petals and stamens are White 155A, the remaining sepals give the open flowers a blush coloration lighter than Red-Purple 62D.

The growth habit and cultural requirements of *Cimicifuga ramosa* 'Hillside Black Beauty' are essentially the same as the parent species, *Cimicifuga ramosa,* although mature height and leaf size are slightly reduced; however, vigor is not noticeably changed. Like the parent species, the plant grows best with ample soil moisture. Leaf color is constant in a sunny or lightly shaded location. The plant is resistant to most diseases and has no insect pests of note. The plant is winter hardy to at least USDA Zone 4. The attribution of Zone 9 hardiness in *The Royal Horticultural Society Dictionary of Gardening, Index of Garden Plants* is incorrect, based on my experience growing the new plant in northwest Connecticut for fifteen (15) years.

The selection has maintained its distinguishing characteristic through successive propagations by tissue culture and by division of the rootstock. All other aspects of the plant are identical to the parent species.

I claim:

1. The new and distinctive cultivar of *Cimicifuga ramosa* plant, substantially as described and illustrated; named 'Hillside Black Beauty', particularly distinguished by the intensive dark purple coloration of the foliage and stems.

* * * * *